United States Patent [19]
Warner et al.

[11] Patent Number: 5,639,280
[45] Date of Patent: Jun. 17, 1997

[54] CONSTRAINING RING FOR A HIP CUP

[75] Inventors: David B. Warner; Stephen G. Gilbert, both of Warsaw, Ind.

[73] Assignee: Zimmer, Inc., Warsaw, Ind.

[21] Appl. No.: 590,028

[22] Filed: Feb. 2, 1996

[51] Int. Cl.⁶ ................................................. A61F 2/32
[52] U.S. Cl. ................................ 623/22; 623/18; 623/20; 623/23
[58] Field of Search .................................. 623/18, 20, 22, 623/23

[56] References Cited

U.S. PATENT DOCUMENTS

| | | | |
|---|---|---|---|
| Re. 31,865 | 4/1985 | Roux | 3/1.912 |
| 3,829,904 | 8/1974 | Ling et al. | 3/128 |
| 3,891,997 | 7/1975 | Herbert | 3/128 |
| 3,903,549 | 9/1975 | Deyerle | 3/1.912 |
| 4,206,517 | 6/1980 | Pappas | 3/1.91 |
| 4,324,006 | 4/1982 | Charnley | 3/1.912 |
| 4,327,449 | 5/1982 | Charnley | 3/1.912 |
| 4,437,193 | 3/1984 | Oh | 3/1.912 |
| 4,479,271 | 10/1984 | Bolesky et al. | 623/18 |
| 4,623,351 | 11/1986 | Church | 623/22 |
| 4,623,352 | 11/1986 | Oh | 623/23 |
| 4,681,589 | 7/1987 | Tronzo | 623/22 |
| 4,715,860 | 12/1987 | Amstutz et al. | 623/22 |
| 4,718,911 | 1/1988 | Kenna | 623/22 |
| 4,743,262 | 5/1988 | Tronzo | 623/22 |
| 4,792,337 | 12/1988 | Muller | 623/22 |
| 4,795,470 | 1/1989 | Goymann | 623/22 |
| 4,834,759 | 5/1989 | Spotorno et al. | 623/22 |
| 4,863,475 | 9/1989 | Andersen et al. | 623/16 |
| 4,955,919 | 9/1990 | Pappas et al. | 623/22 |
| 5,092,897 | 3/1992 | Forte | 623/22 |
| 5,108,445 | 4/1992 | Ashby | 623/11 |

FOREIGN PATENT DOCUMENTS 2 139 098  11/1984  United Kingdom.
2 207 606  2/1989  United Kingdom.

*Primary Examiner*—John G. Weiss
*Assistant Examiner*—Francis K. Cuddihy
*Attorney, Agent, or Firm*—Todd A. Dawson

[57] ABSTRACT

The hip cup of this invention includes a porous metal outer shell, preferably formed from fiber metal, and a compression molded polyethylene component defining an articulating surface at its center for contact with a prosthetic femoral head. The porous outer shell is placed within a mold and the polyethylene component is compression molded within the shell. To prevent the porous shell from collapsing or distorting about its equatorial edge (and thereby distorting the articulating surface) a constraining ring is fitted over the edge of the shell prior to the molding of the polyethylene component. The ring is held in contact with the shell by the molded polyethylene. The constraining ring prevents the edges of the shell from radially distorting during impaction into a prepared acetabulum or during use.

5 Claims, 1 Drawing Sheet

CONSTRAINING RING FOR A HIP CUP

FIELD OF THE INVENTION

This invention relates to prosthetic acetabular components and more specifically relates to a hip cup having a porous outer shell and a molded polyethylene articulating surface wherein a ring contacts the equatorial edge of the outer shell to prevent distortion during use.

SUMMARY OF THE INVENTION

The hip cup of this invention includes a porous metal outer shell, preferably formed from fiber metal, and a compression molded polyethylene component defining an articulating surface at its center for contact with a prosthetic femoral head. The porous outer shell is placed within a mold and the polyethylene component is compression molded within the shell. To prevent the porous shell from collapsing or distorting about its equatorial edge ( and thereby distorting the articulating surface), a constraining ring is fitted over the edge of the shell prior to the molding of the polyethylene component. The ring is held in contact with the shell by the molded polyethylene. The constraining ring prevents the edges of the shell from radially distorting during impaction into a prepared acetabulum or during use.

Accordingly, it is an object of the invention to provide for a novel acetabular hip cup.

Another object of the invention is to provide for a hip cup having a porous shell with a constraining ring positioned adjacent the equatorial edge of the shell to prevent radial distortion of the shell.

Still another object of the invention is to provide for a hip cup having a polyethylene component molded within a porous shell wherein a constraining ring is positioned about the equatorial edge of the shell.

Still other objects of the invention will become apparent upon a reading of the following description taken with the accompanying drawings.

DESCRIPTION OF THE PREFERRED EMBODIMENT

The preferred embodiment herein described is not intended to be exhaustive or to limit the invention to the precise form disclosed. Rather, it is chosen and described to enable others skilled in the art to utilize the teachings of the invention.

Figure 2:
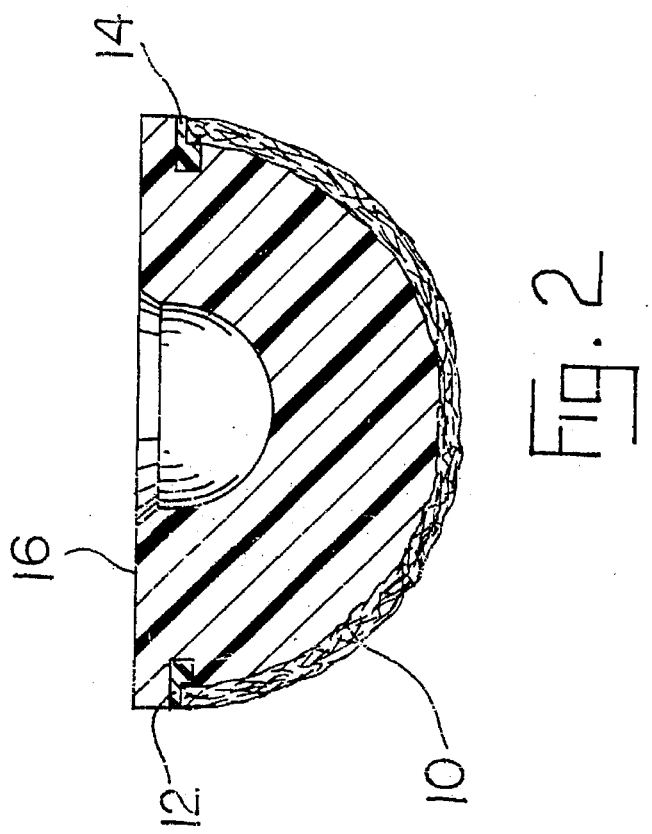
FIG. 2 is a sectional view of the invention illustrating the porous shell, constraining ring, and molded polyethylene component of the invention.
Figure 1:
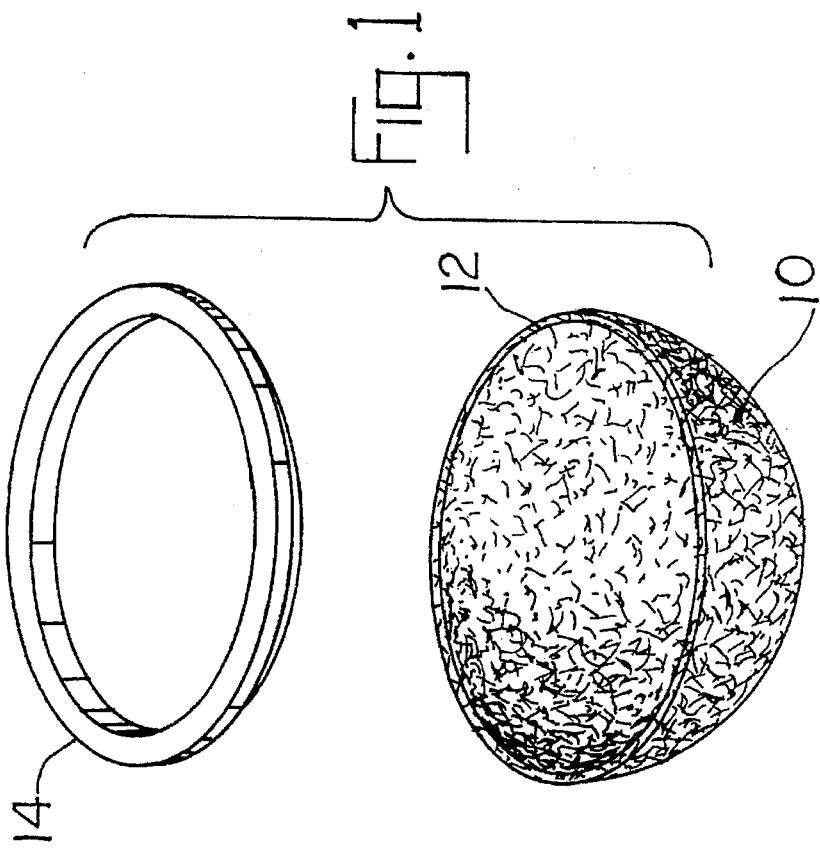
FIG. 1 is an exploded view of a porous metal shell and the constraining ring of the invention.

FIG. 1 illustrates a shell 10 formed from fiber metal in a manner known in the art. Shell 10 defines an equatorial edge 12. A constraining ring 14 is provided and is L-shaped in cross section such that a portion of the ring is positioned interior of edge 12 and a portion is overlying the edge 12 (see FIG. 2). Polyethylene component 16 is molded into the interior of shell 10 by placing shell 10 and ring 14 within the cavity of a mold and filling the shell with polyethylene flake. The flake is compression molded into the shell (using known compression molding techniques) such that a portion of the polyethylene interdigitates with the fiber metal shell. It is preferred that an outermost portion of the shell be filled with a filler material to limit the amount of polyethylene interdigitation. After molding, the filler material may be removed to expose a portion of the porous metal. This method of preventing the complete occlusion of pores within fiber metal is known in the orthopaedic art. As illustrated in FIG. 2, the molded polyethylene component contacts the ring so as to hold the ring in tight contact with the edge 12. As further illustrated, the polyethylene component 16 defines an articulating surface for contact with a prosthetic femoral head (not shown).

In use, when the component is impacted into a prepared acetabulum and during its use within the patient, the constraining ring prevents the shell from collapsing or otherwise distorting about its equatorial edge. Such distortion, if permitted, would distort the articulating surface of the polyethylene component.

It should be understood that the polyethylene component is preferably formed from ultra high molecular weight polyethylene as is commonly used in the field of orthopaedics.

It should be further understood that the invention is not to be limited to the precise form disclosed, but rather may be modified within the keeping of the appended claims.

We claim:

1. A prosthetic acetabular component, said component comprising;

a porous shell being substantially hemispherical and having an equatorial edge, a polyethylene component being molded to the porous shell and overlying the equatorial edge of the shell, and a ring positioned between the polyethylene component and equatorial edge of the shell, said ring contacting an interior of the shell adjacent the equatorial edge, said ring constituting means for preventing distortion of said shell along said equatorial edge.

2. The component of claim 1 wherein said ring has an L-shaped cross section with a portion of the ring overlying the equatorial edge.

3. The component of claim 1 wherein the porous shell is formed from fiber metal.

4. A prosthetic hip cup having a shell formed entirely from fiber metal mesh, the shell defining an equatorial edge, a ring positioned in contact with the shell such that a first portion of the ring overlays the equatorial edge and a second portion contacts the shell at its interior adjacent the equatorial edge, a polyethylene component being molded to and positioned within the interior of the shell and having a portion overlaying said first portion of the ring.

5. A prosthetic acetabular component comprising a porous shell having an equatorial edge and an interior surface, a ring contacting the equatorial edge of the shell and a portion of the interior of the shell adjacent the equatorial edge, a polyethylene component being molded to the shell and being in intimate contact with a substantial portion of the interior of the shell and the ring such that the equatorial edge of the shell is contacted by the ring and the ring is held in position by the polyethylene component, said ring constituting means for preventing distortion of the shell about the equatorial edge.

* * * * *